United States Patent [19]

Shinohara et al.

[11] Patent Number: 5,998,488
[45] Date of Patent: Dec. 7, 1999

[54] OPHTHALMIC COMPOSITION

[75] Inventors: Takashi Shinohara; Yoshikazu Kubo; Shinya Kitoh, all of Tokyo, Japan

[73] Assignee: Lion Corporation, Tokyo, Japan

[21] Appl. No.: 09/141,369

[22] Filed: Aug. 27, 1998

Related U.S. Application Data

[62] Division of application No. 08/579,628, Dec. 26, 1995, abandoned.

[30] Foreign Application Priority Data

Dec. 26, 1994 [JP] Japan .................................. 6-337194

[51] Int. Cl.⁶ ........................... A61K 9/08; A61K 9/107; A61K 47/18; A61K 47/40
[52] U.S. Cl. ............................... 514/839; 514/974
[58] Field of Search ..................... 514/839, 840, 514/912, 914, 915, 974; 424/427

[56] References Cited

U.S. PATENT DOCUMENTS

| | | |
|---|---|---|
| 3,911,107 | 10/1975 | Krezanoski . |
| 4,031,209 | 6/1977 | Krezanoski . |
| 4,470,965 | 9/1984 | Wolf et al. ............................... 514/652 |
| 4,571,039 | 2/1986 | Poler ..................................... 351/160 H |
| 5,318,780 | 6/1994 | Viegas et al. . |
| 5,347,326 | 9/1994 | Volk ....................................... 351/160 R |
| 5,558,876 | 9/1996 | Desai et al. . |
| 5,683,709 | 11/1997 | Yamada et al. .......................... 424/409 |

FOREIGN PATENT DOCUMENTS

| | | |
|---|---|---|
| 0472327A1 | 2/1992 | European Pat. Off. . |
| 472327-A1 | 2/1992 | European Pat. Off. . |
| 4022553 A1 | 1/1992 | Germany . |
| 55-15008B2 | 4/1980 | Japan . |
| 3068503 | 3/1991 | Japan . |

*Primary Examiner*—Robert H. Harrison
*Attorney, Agent, or Firm*—Birch, Stewart, Kolasch & Birch, LLP

[57] ABSTRACT

In an ophthalmic solution comprising an antimicrobial preservative having a quaternary ammonium type cationic group, there are blended a cyclodextrin, EDTA or its salt, and boric acid and/or borax. The solution has an excellent antimicrobial activity and is effective for inhibiting the antimicrobial preservative from adsorbing to contact lenses. It can be instilled to eyes with contact lenses on.

6 Claims, No Drawings

OPHTHALMIC COMPOSITION

This application is a divisional of application No. 08/579,628, filed on Dec. 26, 1995, now abandoned, the entire contents of which are hereby incorporated by reference.

BACKGROUND OF THE INVENTION

1. Field of the Invention

This invention generally relates to an ophthalmic composition comprising an antimicrobial preservative having a cationic group and more particularly, to an ophthalmic composition comprising an antimicrobial preservative having a cationic group which inhibits the antimicrobial preservative from adsorbing to contact lenses while remaining fully antimicrobial.

2. Prior Art

Various antimicrobial preservatives are used in eye drops or ophthalmic solutions. For example, compounds having a cationic group such as benzalkonium chloride, benzethonium chloride, and chlorohexidine gluconate, chlorobutanol, p-aminobenzoates, and sorbic acid are used alone or in admixture of two or more.

Among these antimicrobial preservatives, compounds having a cationic group are widely used in eye drops due to their excellent antimicrobial activity. Undesirably, these antimicrobial preservatives have good affinity to contact lenses, especially soft contact lenses. If an ophthalmic solution containing such an antimicrobial preservative is instilled to an eye with a contact lens put on, the antimicrobial preservative adsorbs to the contact lens. With repeated instillations, the antimicrobial preservative accumulates in the contact lens. The adsorption and accumulation of the antimicrobial preservative can cause chemical and physical degradation of contact lenses. The use of contact lenses having the antimicrobial preservative accumulated therein can cause eye damages.

There is a demand for an ophthalmic solution which can be instilled to eyes without wearing contact lenses, especially soft contact lenses off and which has improved shelf stability. In order to develop such an ophthalmic solution, means for inhibiting the cationic group-bearing antimicrobial preservative from adsorbing to contact lenses is necessary. Various proposals have been made as the anti-adsorption means. For example, Japanese Patent Publication (JP-B) No. 15008/1980 discloses to add a nonionic surfactant to an ophthalmic solution comprising a cationic group-bearing antimicrobial preservative. The nonionic surfactant, however, is not fully effective for inhibiting the antimicrobial preservative from adsorbing to contact lenses. The remaining proposals are also not so successful in providing effective anti-adsorption means.

An object of the present invention is to provide an ophthalmic composition comprising an antimicrobial preservative having a cationic group which not only remains fully antimicrobial, but also inhibits the antimicrobial preservative from adsorbing to contact lenses so that the composition can be instilled to eyes with contact lenses on.

SUMMARY OF THE INVENTION

In connection with an ophthalmic composition comprising an antimicrobial preservative having a cationic group, we have found that by blending a cyclodextrin, ethylenediaminetetraacetic acid or a salt thereof, and boric acid or borax in the composition, the antimicrobial activity of the antimicrobial preservative is not impaired, but rather enhanced and the antimicrobial preservative is effectively prevented from adsorbing to contact lenses, especially soft contact lenses.

Briefly stated, the present invention provides an ophthalmic composition comprising an antimicrobial preservative having a cationic group, a cyclodextrin, ethylenediaminetetraacetic acid or a salt thereof, and boric acid and/or borax.

DETAILED DESCRIPTION OF THE INVENTION

The ophthalmic composition of the invention contains (1) an antimicrobial preservative having a cationic group, (2) a cyclodextrin, (3) ethylenediaminetetraacetic acid or a salt thereof, and (4) boric acid and/or borax as essential components. The composition generally takes the form of a solution containing these components in water.

The antimicrobial preservative having a cationic group used herein may be selected from well-known antimicrobial preservatives, for example, quaternary ammonium salts such as benzalkonium chloride, benzethonium chloride, cetyldimethylbenzylammonium chloride, domiphen bromide, 3-(trimethoxysilyl)propyldimethyloctadecylammonium chloride, stearyldimethylbenzylammonium chloride, stearyltolylmethylammonium chloride, distearyldimethylammonium chloride, stearylpentaethoxyammonium chloride, cetylpyridinium chloride, cetylpyridinium bromide, and lauroylisoquinolium bromide; and guanidines such as chlorohexidine hydrochloride, chlorohexidine gluconate, dodecylguanidine hydrochloride, polyhexmethylenebiguanidine hydrochloride, and 6-acetoxy-2,4-dimethylmetadioxane. These compounds may be used alone or in admixture of two or more. From the standpoints of suitability as eye drops and antimicrobial activity, quaternary ammonium salts are preferable. Among others, benzalkonium chloride is most effective and preferable.

Preferably, the ophthalmic composition of the invention contains 0.001 to 0.1%, more preferably 0.005 to 0.02% of the antimicrobial preservative, based on the entire composition although the antimicrobial preservative content is not critical. Less than 0.001% of the antimicrobial preservative would provide insufficient antimicrobial activity whereas an ophthalmic composition containing more than 0.1% of the antimicrobial preservative would be stimulative to eyes upon instillation and thus provide a less pleasant feel on use.

It is noted that percents are weight/volume percents (wt/vol %) throughout the specification insofar as they represent the contents of components.

The cyclodextrins used herein include cyclodextrins and cyclodextrin derivatives having a saccharide cyclic structure necessary for inclusion. Exemplary cyclodextrins are α-cyclodextrin, β-cyclodextrin, γ-cyclodextrin, and δ-cyclodextrin. Exemplary cyclodextrin derivatives are methylated cyclodextrin, hydroxyethylated cyclodextrin, maltosil-α-cyclodextrin, and triacetyl-β-cyclodextrin. Preferred among these are α-cyclodextrin, β-cyclodextrin, γ-cyclodextrin, δ-cyclodextrin, methylated cyclodextrin, and hydroxyethylated cyclodextrin. They may be used alone or in admixture of two or more.

According to one feature of the invention, the cyclodextrin is added to an ophthalmic composition containing a cationic group-bearing antimicrobial preservative for restraining the antimicrobial preservative from adsorbing to contact lenses. Preferably, the ophthalmic composition of the invention contains 0.03 to 1%, more preferably 0.03 to 0.5% of the cyclodextrin, based on the entire composition although the cyclodextrin content is not critical. Less than 0.03% of the cyclodextrin would be less effective for inhibiting the antimicrobial preservative from adsorption whereas more than 1% of the cyclodextrin would detract from the shelf stability of an ophthalmic composition at low temperature.

The salt of ethylenediaminetetraacetic acid (EDTA) may be selected from well-known salts, for example, alkali metal salts of EDTA such as potassium EDTA (EDTA-2K), tripotassium EDTA, sodium zinc EDTA, disodium EDTA (EDTA-2Na), trisodium EDTA, tetrasodium EDTA, sodium calcium EDTA, sodium cobalt EDTA, sodium iron EDTA, sodium copper EDTA, sodium nickel EDTA, sodium magnesium EDTA, and sodium manganese EDTA; and ammonium EDTA and ammonium iron EDTA. The alkali metal salts are preferred. They may be used alone or in admixture of two or more. The salt may also be used in combination with EDTA.

By the combined use of a cyclodextrin and EDTA or EDTA salt, the invention prevents any lowering of antimicrobial activity of the ophthalmic composition by the cyclodextrin. Although the content of EDTA or salt is not critical, the ophthalmic composition of the invention preferably contains at least 0.006%, more preferably 0.006 to 0.1%, most preferably 0.006 to 0.06% of EDTA or salt, based on the entire composition. Less than 0.006% of EDTA would be less effective for preventing any lowering of antimicrobial activity of the ophthalmic composition. More than 0.1% of EDTA would be stimulative to eyes upon instillation and thus provide a less pleasant feel on use.

In addition to the above-mentioned components, the ophthalmic composition of the invention further contains boric acid or borax or both. Boric acid or borax is effective for enhancing the antimicrobial activity of the composition. Boric acid and borax need not be used in admixture although their combined use is more effective. Although the contents of boric acid and borax are not critical, the content of boric acid is at least 0.1% and the content of borax is at least 0.01%, based on the entire composition. Below these levels, boric acid or borax would be less effective for enhancing the antimicrobial activity. From the standpoint of safety to human bodies, their contents are preferably as low as possible and therefore, the content of boric acid is preferably 0.1 to 0.5% and the content of borax is 0.01 to 0.08%.

The ophthalmic composition may be used in any desired application as both treating eye drops and general eye drops. Since the ophthalmic composition of the invention is devised such that the antimicrobial preservative may not adsorb to contact lenses, it is most useful as a contact lens-compatible ophthalmic solution which can be instilled to eyes with contact lenses, especially soft contact lens put on.

In addition to the above-mentioned components, the ophthalmic composition of the invention may further contain suitable amounts of various components commonly used in the preparation of eye drops, if desired. For example, there may be contained active components such as anti-inflammatory agents, vitamins, and antihystaminics and additives such as pH adjusting agents, buffer agents, isotonic agents, solubilizing agents, and preservatives.

The ophthalmic composition of the invention is fully effective for restraining the antimicrobial preservative from adsorbing to contact lenses, especially soft contact lenses, without detracting from the antimicrobial activity of the antimicrobial preservative. The invention rather offers better antimicrobial activity than conventional ophthalmic compositions containing a cationic group-bearing antimicrobial preservative. Therefore, the ophthalmic composition of the invention is most useful as a contact lens-compatible ophthalmic solution which can be instilled to eyes without removing contact lenses, especially soft contact lens.

EXAMPLE

Examples of the present invention are given below by way of illustration and not by way of limitation.

Experiment 1

A test was conducted to examine the inhibition of benzalkonium chloride adsorption to soft contact lenses. Solutions of the following formulation were prepared in a conventional manner as used in the preparation of eye drops.

Formulation

| Components | % |
| --- | --- |
| Taurine | 1 |
| Sodium dihydrogen phosphate | 0.7 |
| Disodium hydrogen phosphate | 0.06 |
| α-cyclodextrin | 0.01–0.3 |
| Benzalkonium chloride | 0.01 |
| Sterile purified water | balance |
| | 100.0 |

The percent inhibition of benzalkonium chloride adsorption to commercially available soft contact lenses was determined by the following test. The results are shown in Table 1.

Benzalkonium chloride adsorption test A 30-ml vial was charged with 10 ml of the solution and a soft contact lens was immersed therein. In a constant temperature tank at 25° C., the vial was shaken for 24 hours. After the contact lens was removed from the vial, the concentration of benzalkonium chloride in the solution was quantitatively determined by high performance liquid chromatography. A percent inhibition of adsorption was calculated according to the following formula.

As a control, the above procedure was repeated except that no contact lens was immersed.

Inhibition of adsorption (%)=(concentration of benzalkonium chloride in sample solution)/(concentration of benzalkonium chloride in control solution)×100

TABLE 1

| Soft contact lens | α-cyclodextrin concentration (%) | | | | | | | |
| --- | --- | --- | --- | --- | --- | --- | --- | --- |
| | 0 | 0.01 | 0.02 | 0.03 | 0.05 | 0.1 | 0.2 | 0.3 |
| Seequence | 65 | 88 | 92 | 100 | 100 | 100 | 100 | 100 |
| Nichicon Soft μ | 60 | 87 | 93 | 100 | 100 | 100 | 100 | 100 |
| Menicon Soft 72 | 65 | 88 | 92 | 100 | 100 | 100 | 100 | 100 |

Note that Seequence, Nichicon Soft and Menicon Soft are trademarks of soft contact lenses commercially available from Bausch & Lomb, Nihon Contact K.K., and Menicon K.K., respectively.

It is evident from Table 1 that the adsorption of benzalkonium chloride to soft contact lenses is inhibited by adding α-cyclodextrin to a solution containing benzalkonium chloride. The inhibition effect is remarkable when α-cyclodextrin is added to a solution in a sufficient amount to give a concentration of at least 0.03%.

Approximately equivalent results were obtained when α-cyclodextrin was replaced by β-cyclodextrin, γ-cyclodextrin, δ-cyclodextrin, methylated cyclodextrin, and hydroxy-ethylated cyclodextrin.

Experiment 2

The above solutions were examined for low-temperature stability. More specifically, solutions were prepared in accordance with the formulation shown in Experiment 1 while the amount of α-cyclodextrin mixed was in the range of 0.03 to 2%. The solutions were allowed to stand for 6 months at 50° C. before their appearance was observed to evaluate the stability according to the following criterion. The results are shown in Table 2.

Evaluation criterion

O: no change

δ: slightly turbid

X: precipitated

TABLE 2

| Cyclodextrin concentration (%) | Stability |
|---|---|
| 0.03 | O |
| 0.5 | O |
| 1 | Δ |
| 2 | X |

It is evident from Tables 1 and 2 that the adsorption of benzalkonium chloride to soft contact lenses is inhibited by adding a-cyclodextrin to a solution containing benzalkonium chloride and that the concentration of α-cyclodextrin should preferably be up to 1%, more preferably up to 0.5% when the low-temperature stability of the solution is taken into account. Similar results were obtained with other cyclodextrins.

Experiment 3

The solutions of Experiment 1 were subject to an antimicrobial test.

Antimicrobial test

Using bacteria *Escherichia coli* (*E. coli*), *Pseudomonas aeruginosa* (*P. aeru*), and *Stapyrococcus aureus* (*S. aureus*) and fungi *Aspergillus nigar* (*A. nigar*) and *Candida albicans* (Candida) as infectious microorganisms, a preservative effectiveness test was carried out according to the Pharmacopoeia of the United States.

The test results were evaluated according to the following criteria. The results are shown in Table 3.

++: microorganisms died within 5 days

+: microorganisms died in 6–10 days

−: microorganisms died in 11–15 days or over 15 days

TABLE 3

| | α-cyclodextrin concentration (%) | | | | | | |
|---|---|---|---|---|---|---|---|
| Microorganism | 0.01 | 0.02 | 0.03 | 0.05 | 0.1 | 0.2 | 0.3 |
| *E. coli* | + | + | − | − | − | − | − |
| *P. aeru* | + | + | − | − | − | − | − |
| *S. aureus* | + | + | − | − | − | − | − |
| *A. nigar* | + | + | − | − | − | − | − |
| Candida | + | + | − | − | − | − | − |

It is evident from Tables 1 and 3 that when α-cyclodextrin is added to a solution containing benzalkonium chloride so as to provide a concentration of 0.03% or more, the adsorption of benzalkonium chloride to soft contact lenses is inhibited, but the solution is significantly reduced in antimicrobial activity.

Experiment 4

Solutions were prepared in accordance with the formulation shown in Experiment 1 in a conventional manner as used in the preparation of eye drops while the amount of disodium ethylenediaminetetraacetate (EDTA-2Na) blended was in the range of 0.002 to 0.3%. The solutions were subject to the antimicrobial test of Experiment 3 and evaluated for antimicrobial activity according to the same criterion as above. The results are shown in Table 4. Since the results were the same for all types of microorganism, the type of microorganism is not specified in Table 4.

TABLE 4

| α-cyclo- | EDTA-2Na concentration (%) | | | | | | |
|---|---|---|---|---|---|---|---|
| dextrin (%) | 0.002 | 0.004 | 0.006 | 0.01 | 0.05 | 0.1 | 0.3 |
| 0.01 | + | + | + | + | + | + | + |
| 0.03 | − | − | + | + | + | + | + |
| 0.05 | − | − | + | + | + | + | + |
| 0.1 | − | − | + | + | + | + | + |
| 0.3 | − | − | + | + | + | + | + |
| 0.5 | − | − | + | + | + | + | + |
| 1.0 | − | − | + | + | + | + | + |

It is evident from Table 4 that addition of EDTA-2Na prevents a lowering of antimicrobial activity of a solution containing benzalkonium chloride by addition of 0.01 to 1.0% of α-cyclodextrin. The effect becomes remarkable when the concentration of EDTA-2Na in the solution is at least 0.006%.

Experiment 5

Solutions of the following formulation were prepared in a conventional manner as used in the preparation of eye drops.

| Formulation | |
|---|---|
| Components | % |
| Taurine | 1.0 |
| EDTA-2Na | 0.006 |
| α-cyclodextrin | 0.03 |
| Benzalkonium chloride | 0.01 |
| Boric acid | 0–1.0 |
| Borax | 0–0.15 |
| Sodium dihydrogen phosphate | proper amount* |
| Disodium hydrogen phosphate | proper amount* |
| Sterile purified water | balance |
| | 100.0 |

*Sodium dihydrogen phosphate and disodium hydrogen phosphate were added in proper amounts to adjust the ophthalmic solution at about pH 7.2.

The solutions were subject to the antimicrobial test of Experiment 3 and evaluated for antimicrobial activity according to the same criterion as above. The results are shown in Table 5. Since the results were the same for all types of microorganism, the type of microorganism is not specified in Table 5.

TABLE 5

| Borax (%) | Boric acid (%) | | | | | | | |
|---|---|---|---|---|---|---|---|---|
| | 0 | 0.05 | 0.1 | 0.2 | 0.4 | 0.6 | 0.8 | 1.0 |
| 0 | | + | + | ++ | ++ | ++ | ++ | ++ | ++ |
| 0.01 | + | + | ++ | ++ | ++ | ++ | ++ | ++ |
| 0.02 | + | + | ++ | ++ | ++ | ++ | ++ | ++ |
| 0.04 | + | + | ++ | ++ | ++ | ++ | ++ | ++ |
| 0.06 | + | + | ++ | ++ | ++ | ++ | ++ | ++ |
| 0.08 | + | + | ++ | ++ | ++ | ++ | ++ | ++ |
| 0.1 | + | + | ++ | ++ | ++ | ++ | ++ | ++ |
| 0.15 | ++ | ++ | ++ | ++ | ++ | ++ | ++ | ++ |

It is evident from Table 5 that boric acid and borax, whether they are used alone or in admixture, are effective for enhancing the antimicrobial activity of solutions containing benzalkonium chloride, α-cyclodextrin, and EDTA-2Na. Particularly when boric acid is added in a concentration of at least 0.1% and borax is added in a concentration of at least 0.01%, the solutions are significantly improved in antimicrobial activity.

In general, boric acid and borax are often used in conventional ophthalmic solutions in concentrations of about 0.5 to 1.0%. In the ophthalmic solution of the invention, boric acid and borax exert their antimicrobial activity improving effect at lower concentrations (for example, 0.1%). From the standpoint of human body safety, the inventive ophthalmic solution is more favorable than the conventional ophthalmic solutions.

Example 1 and Comparative Examples 1–2

Solutions of the formulation shown in Table 6 were prepared to a total amount of 1,000 g in a conventional manner as used in the preparation of eye drops. Ophthalmic solutions of Example 1 and Comparative Examples 1 and 2 were obtained. The ophthalmic solutions were subject to the same tests as in Experiments 1 and 3. In the test of Experiment 3, the ophthalmic solutions were evaluated for antimicrobial activity according to the same criterion as before. The results are also shown in Table 6.

TABLE 6

| Component (%) | E 1 | CE 1 | CE 2 |
|---|---|---|---|
| Taurine | 1.0 | 1.0 | 1.0 |
| EDTA-2Na | 0.01 | 0 | 0.01 |
| α-cyclodextrin | 0.03 | 0.03 | 0.03 |
| Benzalkonium chloride | 0.01 | 0.01 | 0.01 |
| Sodium dihydrogen phosphate | 0 | 0.6 | 0.6 |
| Disodium hydrogen phosphate | 0 | 0.07 | 0.07 |
| Boric acid/borax | 0.6/0.7 | 0 | 0 |
| Sterile purified water | balance | balance | balance |
| total | 100.0 | 100.0 | 100.0 |
| Inhibition of adsorption (%) | | | |
| Seequence | 100 | 100 | 100 |
| Nichion Soft μ | 100 | 100 | 100 |
| Menicon Soft 72 | 100 | 100 | 100 |
| Antimicrobial activity | | | |
| E. coli | ++ | − | + |
| P. aeru | ++ | − | + |
| S. aureus | ++ | − | + |
| A. nigar | ++ | − | + |
| Candida | ++ | − | + |

It is evident from Table 6 that when an ophthalmic solution containing benzalkonium chloride is mixed with α-cyclodextrin, EDTA-2Na, boric acid, and borax (Example 1), the resulting solution has an excellent antimicrobial activity. In contrast, when an ophthalmic solution containing benzalkonium chloride is mixed with only α-cyclodextrin, the resulting solution has an increased inhibition effect for antimicrobial preservative adsorption, but a low antimicrobial activity.

Examples 2–13

Solutions of the formulation shown in Table 7 were prepared to a total amount of 1,000 g in a conventional manner as used in the preparation of eye drops. Ophthalmic solutions of Examples 2 to 13 were obtained. The ophthalmic solutions were subject to the same tests as in Experiments 1 and 3. In the test of Experiment 3, the ophthalmic solutions were evaluated for antimicrobial activity according to the same criterion as before. The results are also shown in Table 7.

TABLE 7

| Component (%) | Examples | | | | | | | | | | | |
|---|---|---|---|---|---|---|---|---|---|---|---|---|
| | 2 | 3 | 4 | 5 | 6 | 7 | 8 | 9 | 10 | 11 | 12 | 13 |
| Taurine | 1 | 1 | 1 | 1 | 1 | 1 | 1 | 1 | — | — | — | 1 |
| Sodium chondroitin sulfate | — | 0.5 | — | 0.5 | 0.5 | 0.3 | 0.5 | 0.5 | 0.5 | 0.5 | 0.5 | 0.5 |
| NaCl | — | — | 0.5 | 0.5 | 0.5 | 0.5 | — | 0.2 | 0.5 | 0.5 | 0.5 | 0.5 |
| KCl | — | — | — | 0.05 | — | 0.05 | — | — | 0.05 | 0.1 | 0.1 | 0.05 |
| Benzalkonium chloride | 0.01 | 0.01 | 0.01 | 0.01 | 0.01 | 0.01 | 0.01 | 0.01 | 0.01 | — | — | 0.01 |
| Chlorohexidine gluconate | — | — | — | — | — | — | — | — | — | 0.01 | — | — |
| Benzethonium chloride | — | — | — | — | — | — | — | — | — | — | 0.01 | — |
| Boric acid | 1 | 1 | 0.6 | 0.7 | 0.6 | 0.55 | 0.3 | 0.7 | 0.6 | 0.5 | 0.5 | 0.7 |
| Borax | 0.1 | 0.1 | 0.07 | 0.08 | 0.07 | 0.05 | 0.02 | 0.07 | 0.07 | 0.06 | 0.06 | 0.08 |
| α-cyclodextrin | 0.05 | 0.1 | 0.1 | 0.15 | — | — | — | — | 0.1 | 0.1 | — | 0.15 |
| β-cyclodextrin | — | — | — | — | 0.15 | — | — | — | 0.1 | 0.1 | — | — |
| γ-cyclodextrin | — | — | — | — | — | 0.1 | — | — | 0.1 | 0.1 | 0.15 | — |
| Methylated α-cyclodextrin | — | — | — | — | — | — | 0.15 | — | 0.1 | 0.1 | — | — |
| Hydroxyethylated β-cyclodextrin | — | — | — | — | — | — | — | 0.1 | 0.1 | 0.1 | — | — |
| EDTA-2Na | 0.006 | 0.01 | 0.01 | 0.05 | 0.05 | 0.01 | 0.1 | 0.05 | 0.05 | 0.05 | 0.05 | — |
| EDTA-2K | — | — | — | — | — | — | — | — | — | — | — | 0.05 |
| Inhibition of adsorption (%) | 100.1 | 99.3 | 100.1 | 99.7 | 99.1 | 99.5 | 99.0 | 99.5 | 99.3 | 99.2 | 99.3 | 99.7 |
| Antimicrobial activity | ++ | ++ | ++ | ++ | ++ | ++ | ++ | ++ | ++ | ++ | ++ | ++ |

Japanese Patent Application No. 337194/1994 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for inhibiting antimicrobial preservative from adsorbing to contact lens, which comprises:
    administering to an eye of a person wearing the contact lens an ophthalmic composition consisting essentially of:
        an antimicrobial preservative having a cationic group;
        a cyclodextrin;
        ethylenenediaminetetraacetic acid or a salt thereof;
        at least one of boric acid and borax; and
        optionally, at least one member selected from the group consisting of: anti-inflammatory agents, vitamins, antihystaminics, pH adjusting agents, buffer agents, isotonic agents, solubilizing agents, preservatives and taurine.

2. The method of claim 1, wherein said contact lens is a soft contact lens.

3. The method of claim 1, wherein said antimicrobial preservative having a cationic group is a quaternary ammonium cationic surfactant.

4. The method of claim 3, wherein said quaternary ammonium cationic surfactant is benzalkonium chloride.

5. The method of claim 1, wherein said ophthalmic composition is an aqueous solution consisting essentially of
    0.03 to 1 wt/vol % of the cyclodextrin,
    at least 0.006 wt/vol % of ethylenediaminetetraacetic acid or a salt thereof,
    at least 0.1 wt/vol % of boric acid, and
    at least 0.01 wt/vol % of borax, wherein each wt/vol % is based on all components of the composition.

6. A method for treating an eye of a contact lens user which comprises administering to an eye of a person wearing a contact lens an ophthalmic composition consisting essentially of:
    an antimicrobial preservative having a cationic group;
    a cyclodextrin;
    ethylenenediaminetetraacetic acid or a salt thereof;
    at least one of boric acid and borax; and optionally, at least one member selected from the group consisting of: anti-inflammatory agents, vitamins, antihystaminics, pH adjusting agents, buffer agents, isotonic agents, solubilizing agents, preservatives and taurine.

* * * * *